(12) United States Patent
Barolat et al.

(10) Patent No.: US 7,848,818 B2
(45) Date of Patent: *Dec. 7, 2010

(54) SYSTEM AND METHOD FOR NEUROLOGICAL STIMULATION OF PERIPHERAL NERVES TO TREAT LOW BACK PAIN

(76) Inventors: Giancarlo Barolat, 730 Genesee Mountain Rd., Golden, CO (US) 80401; Tracy L Cameron, 18 Norma Crescent, Toronto, ON (CA) M6P 3H1; Christopher G Chavez, 2900 Cedar Ridge Dr., McKinney, TX (US) 75070

( * ) Notice: Subject to any disclaimer, the term of this patent is extended or adjusted under 35 U.S.C. 154(b) by 345 days.

This patent is subject to a terminal disclaimer.

(21) Appl. No.: 11/948,134

(22) Filed: Nov. 30, 2007

(65) Prior Publication Data

US 2008/0188906 A1    Aug. 7, 2008

Related U.S. Application Data

(63) Continuation of application No. 11/066,669, filed on Feb. 25, 2005, now Pat. No. 7,324,852.

(60) Provisional application No. 60/547,506, filed on Feb. 25, 2004.

(51) Int. Cl.
*A61N 1/36* (2006.01)
(52) U.S. Cl. ...................................................... 607/46
(58) Field of Classification Search ............... 607/2, 607/46, 117, 118
See application file for complete search history.

(56) References Cited

U.S. PATENT DOCUMENTS

| 5,417,719 | A  | * | 5/1995 | Hull et al. ............. 607/46 |
| 6,505,075 | B1 | * | 1/2003 | Weiner ................. 607/46 |
| 7,324,852 | B2 | * | 1/2008 | Barolat et al. ......... 607/46 |
| 2003/0078633 | A1 | * | 4/2003 | Firlik et al. .......... 607/46 |
| 2005/0240243 | A1 |   | 10/2005 | Barolat et al. |
| 2005/0246006 | A1 | * | 11/2005 | Daniels ............... 607/117 |
| 2006/0025832 | A1 | * | 2/2006 | O'Keeffe et al. ....... 607/46 |
| 2007/0021801 | A1 | * | 1/2007 | Heruth et al. ......... 607/46 |

* cited by examiner

*Primary Examiner*—Carl H Layno
*Assistant Examiner*—Brian T Gedeon
(74) *Attorney, Agent, or Firm*—Melissa Acosta; Christopher S. L. Crawford; Peter Lando

(57) ABSTRACT

According to one embodiment, a system for neurological stimulation of peripheral nerve fibers to treat low back pain is provided. The system includes stimulation electrodes adapted to be implanted in tissue proximate a network of peripheral nerve fibers located in and innervating a painful region of the low back area and to deliver electrical stimulation pulses to the network of peripheral nerve fibers located in and innervating the painful region of the low back area. The system also includes a stimulation source adapted for implantation into the person's body and operable to generate electrical stimulation pulses for transmission to the electrodes for delivery to the network of peripheral nerve fibers located in and innervating the painful region of the low back area to relieve pain in the painful region of the low back area.

7 Claims, 8 Drawing Sheets

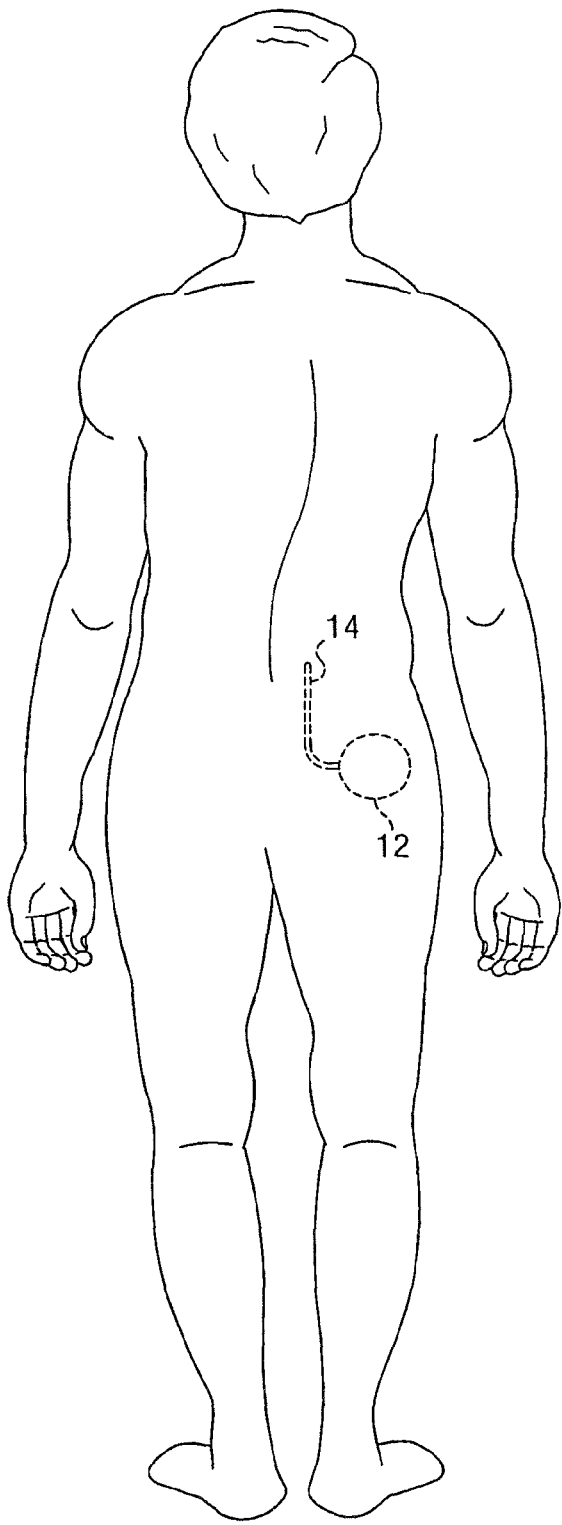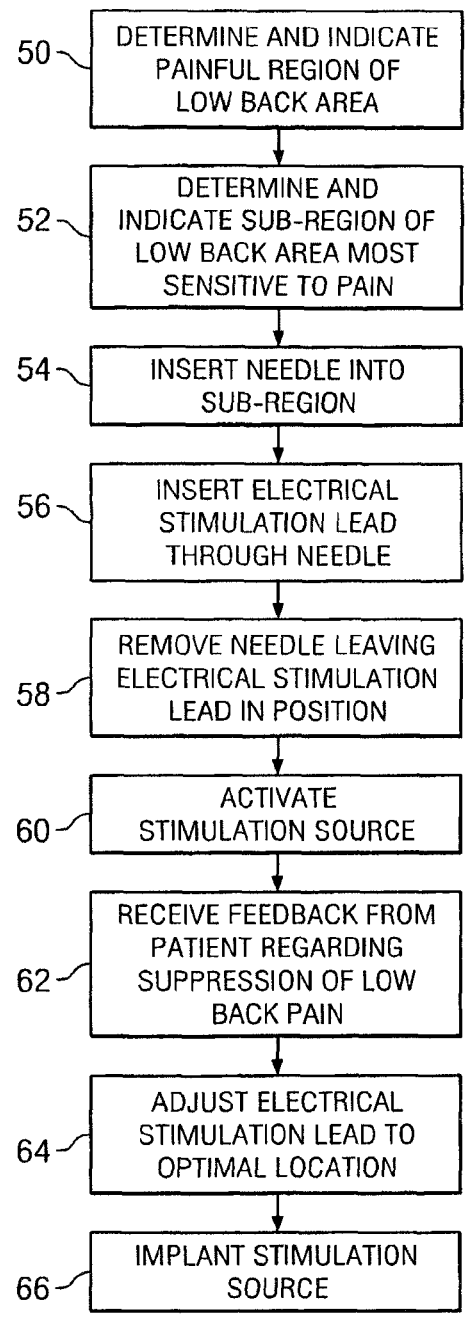
FIG. 3
FIG. 4

SYSTEM AND METHOD FOR NEUROLOGICAL STIMULATION OF PERIPHERAL NERVES TO TREAT LOW BACK PAIN

RELATED APPLICATIONS

This application claims the benefit as a continuation of U.S. application Ser. No. 11/066,669, filed Feb. 25, 2005, now U.S. Pat. No. 7,324,852, which claims benefit of U.S. Provisional Application Ser. No. 60/547,506, filed Feb. 25, 2004.

TECHNICAL FIELD

This invention relates generally to therapeutic neurological stimulation and in particular to a system and method for neurological stimulation of peripheral nerves to treat low back pain.

BACKGROUND

Neurological stimulation may be applied to specifically targeted nerve tissue in the spinal cord or a particular identified peripheral nerve to treat regions of the body affected by chronic pain from a variety of etiologies. According to one technique, a set of efficacious neurological stimulation parameters are determined, the set of parameters is entered into a stimulation system, and the stimulation system is used to electrically or chemically stimulate the specifically targeted nerve tissue in the spinal cord or particular identified peripheral nerve according to the set of stimulation parameters.

For electrical stimulation, typically, an implanted pulse generator transmits a pulse of electrical energy to an implanted electrical stimulation lead according to the set of stimulation parameters and, in response to the pulse, the electrodes of the implanted stimulation lead deliver the electrical energy to the specifically targeted nerve tissue in the spinal cord or particular identified peripheral nerve. The electrical energy stimulates the specifically targeted nerve tissue in the spinal cord or particular identified peripheral nerve to cause a subjective sensation of numbness or tingling in the affected region of the body, known as "paresthesia," which masks or otherwise relieves pain in the affected region. For example, the electrodes may be located external to the dura adjacent the specifically targeted nerve tissue in the spinal cord that is to be stimulated. The electrodes typically must be precisely positioned based on the location of the specifically targeted nerve tissue in the spinal cord or particular identified peripheral nerve.

Alternatively, for chemical stimulation, typically, an implantable drug pump transmits a pulse of medication through an infusion catheter according to the set of stimulation parameters and, in response to the pulse, infusion ports of the implanted infusion catheter deliver the medication to the specifically targeted nerve tissue in the spinal cord or particular identified peripheral nerve. The medication stimulates the specifically targeted nerve tissue in the spinal cord or particular identified peripheral nerve to mask or otherwise relieve pain in the affected region of the body. The infusion ports typically must be precisely positioned based on the location of the specifically targeted nerve tissue in the spinal cord or particular peripheral nerve that is to be stimulated.

Of course, in many cases, chronic pain may be intractable other than through highly invasive surgical procedures. For example, for chronic pain in the low back area associated with a herniated disc, a discectomy or other radical surgery may be required for adequate pain relief. However, such highly invasive surgical procedures involve a host of undesirable consequences. These may include the significant cost of the surgery itself, the risk of paralysis or death due to complications during surgery, the trauma to the skin, muscles, nerves, and associated anatomical structures and the resulting scarring, pain, and discomfort that naturally results from the surgery, the significant rehabilitation time and associated costs following the surgery, and other consequences. Perhaps worse, such highly invasive surgical procedures often do not even completely suppress the chronic pain for which they were indicated.

SUMMARY OF THE INVENTION

Certain embodiments of the present invention may reduce or eliminate certain problems and disadvantages associated with previous techniques for treating low back pain. Although treatment of low back pain is primarily described, clinical results indicate that embodiments of the present invention may involve treatment of virtually any painful region of the trunk or limbs.

According to one embodiment, a system for neurological stimulation of peripheral nerve fibers to treat low back pain is provided. The system includes stimulation electrodes adapted to be implanted in tissue proximate a network of peripheral nerve fibers located in and innervating a painful region of the low back area and to deliver electrical stimulation pulses to the network of peripheral nerve fibers located in and innervating the painful region of the low back area. The system also includes a stimulation source adapted for implantation into the person's body and operable to generate electrical stimulation pulses for transmission to the electrodes for delivery to the network of peripheral nerve fibers located in and innervating the painful region of the low back area to relieve pain in the painful region of the low back area.

Particular embodiments of the present invention may provide one or more technical advantages. Certain embodiments may provide all, some, or none of these advantages. Certain embodiments may provide one or more other advantages, one or more of which may be readily apparent to those skilled in the art from the figures, descriptions, and claims included herein.

In certain embodiments, an implanted neurological stimulation system is used to electrically stimulate a network of peripheral nerve fibers located in and innervating the low back area to treat low back pain. In particular, electrodes are implanted inside a person's body in tissue surrounding, overlying, or otherwise proximate the network of peripheral nerve fibers located in and innervating the painful region of the low back area. For example, the electrodes may be located in the epidermis, the dermis, or the subcutaneous tissue surrounding, overlying, or otherwise proximate the network of peripheral nerve fibers located in and innervating the painful region of the low back area. The electrodes deliver electrical stimulation pulses to the network of peripheral nerve fibers located in and innervating the painful region of the low back area, which may provide paresthesia or otherwise partially or completely suppress the person's pain in the painful region of the low back area, which may in turn significantly increase the person's quality of life. For example, where a person suffers from chronic intractable pain due to surgery, trauma, or other stress to the bones, musculature, nerves, or other anatomical structures in the low back area, the electrodes may deliver electrical stimulation pulses to the network of peripheral nerve fibers located in and innervating the painful region of the low back area to relieve pain in the painful region of the low back area.

In contrast to prior techniques for treating low back pain requiring highly invasive surgery, certain embodiments of the present invention may allow chronic intractable pain to be successfully treated without invasive surgical procedures and their associated negative consequences, providing an important technical advantage. Furthermore, in contrast to prior techniques for treating pain in a particular region of the body requiring the electrical stimulation lead to be implanted adjacent the spinal cord or a particular identified peripheral nerve such that the electrodes are precisely located proximate specifically targeted nerve tissue in the spinal cord or the particular identified peripheral nerve, certain embodiments of the present invention allow the lead to be implanted in tissue surrounding, overlying, or otherwise proximate a network of peripheral nerve fibers located in and innervating the painful region of the low back area without regard to the precise location of particular nerve tissue in the spinal cord or any particular identified peripheral nerve. Among other benefits, for example, this may make implanting the electrical stimulation lead and locating the electrodes easier for the doctor and safer for the patient, providing an important technical advantage.

In certain embodiments, a neurological stimulation system is used to deliver a medication or other chemical to the network of peripheral nerve fibers located in and innervating the painful region of the low back area using an implanted infusion pump and catheter to chemically stimulate the network of peripheral nerve fibers located in and innervating the painful region of the low back area to relieve pain in the low back area, in conjunction with or independent from any electrical stimulation of the network of peripheral nerve fibers located in and innervating the painful region of the low back area.

BRIEF DESCRIPTION OF THE DRAWINGS

For a more complete understanding of the present invention and advantages thereof, reference is now made to the following description taken in conjunction with the accompanying drawings, in which:

FIG. 3 illustrates example placement of the electrical stimulation system shown in FIGS. 1A-1B within a person's body;

FIG. 4 illustrates an example method for implanting the stimulation system of FIGS. 1A-1B into a person to stimulate peripheral nerves to treat low back pain;

DESCRIPTION OF EXAMPLE EMBODIMENTS

Figure 1A:
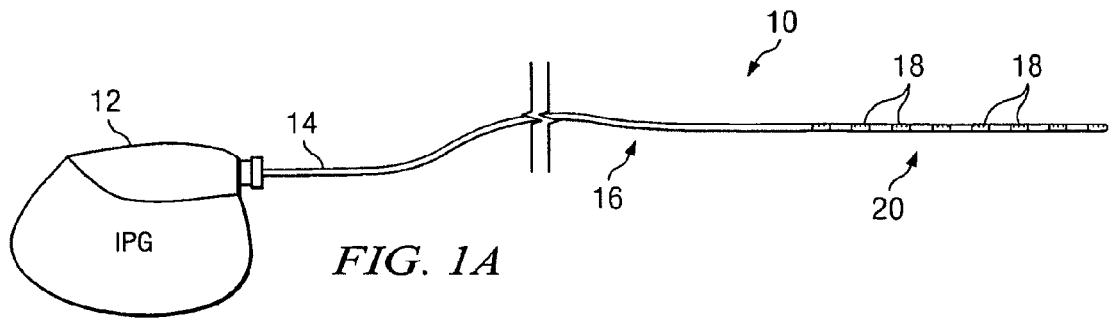
FIGS. 1A-1B illustrate example systems for neurological stimulation of peripheral nerves to treat low back pain.

According to the present invention, a neurological stimulation system is used to stimulate peripheral nerves in a painful region of the low back area to treat low back pain. Although treatment of low back pain is primarily described, clinical results indicate that embodiments of the present invention may involve treatment of virtually any painful region of the trunk or limbs.

In certain embodiments, an implanted neurological stimulation system is used to electrically stimulate a network of peripheral nerve fibers located in and innervating the low back area to treat low back pain. In particular, electrodes are implanted inside a person's body in tissue surrounding, overlying, or otherwise proximate the network of peripheral nerve fibers located in and innervating the painful region of the low back area. For example, the electrodes may be located in the epidermis, the dermis, or the subcutaneous tissue surrounding, overlying, or otherwise proximate the network of peripheral nerve fibers located in and innervating the painful region of the low back area. The electrodes deliver electrical stimulation pulses to the network of peripheral nerve fibers located in and innervating the painful region of the low back area, which may provide paresthesia or otherwise partially or completely suppress the person's pain in the painful region of the low back area, which may in turn significantly increase the person's quality of life. For example, where a person suffers from chronic intractable pain due to surgery, trauma, or other stress to the bones, musculature, nerves, or other anatomical structures in the low back area, the electrodes may deliver electrical stimulation pulses to the network of peripheral nerve fibers located in and innervating the painful region of the low back area to relieve pain in the painful region of the low back area.

In contrast to prior techniques for treating low back pain requiring highly invasive surgery, certain embodiments of the present invention may allow chronic intractable pain to be successfully treated without invasive surgical procedures and their associated negative consequences, providing an important technical advantage. Furthermore, in contrast to prior techniques for treating pain in a particular region of the body requiring the electrical stimulation lead to be implanted adjacent the spinal cord or a particular identified peripheral nerve such that the electrodes are precisely located proximate specifically targeted nerve tissue in the spinal cord or the particular identified peripheral nerve, certain embodiments of the present invention allow the lead to be implanted in tissue surrounding, overlying, or otherwise proximate a network of peripheral nerve fibers located in and innervating the painful region of the low back area without regard to the precise location of particular nerve tissue in the spinal cord or any particular identified peripheral nerve. Among other benefits, for example, this may make implanting the electrical stimulation lead and locating the electrodes easier for the doctor and safer for the patient, providing an important technical advantage.

In certain embodiments, a neurological stimulation system is used to deliver a medication or other chemical to the network of peripheral nerve fibers located in and innervating the painful region of the low back area using an implanted infusion pump and catheter to chemically stimulate the network of peripheral nerve fibers located in and innervating the painful region of the low back area to relieve pain in the low back area, in conjunction with or independent from any electrical stimulation of the network of peripheral nerve fibers located in and innervating the painful region of the low back area.

Figure 1B:
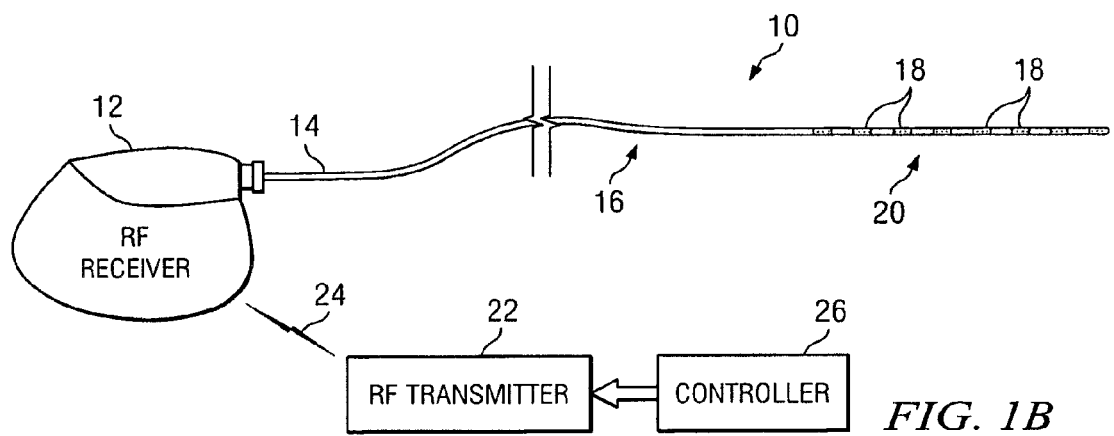

FIGS. 1A-1B illustrate example systems 10 for neurological stimulation of peripheral nerves to treat low back pain. Stimulation system 10 generates and applies a stimulus to a network of peripheral nerve fibers located in and innervating a painful region of the low back area to relieve pain in the painful region of the low back area. In general terms, stimulation system 10 includes an implantable electrical stimulation source 12 and one or more implantable electrical stimulation leads 14 for applying electrical stimulation pulses to the network of peripheral nerve fibers located in and innervating the painful region of the low back area. In operation, both of these primary components are implanted in the person's body, as discussed below with reference to FIGS. 3, 4, and 5A-5E. In certain embodiments, stimulation source 12 is coupled directly to a connecting portion 16 of electrical stimulation lead 14. In certain other embodiments, stimulation source 12 is not coupled directly to stimulation lead 14 and stimulation source 12 instead communicates with stimulation lead 14 via a wireless link. In certain other embodiments, stimulation source 12 and electrodes 18 are contained in an "all-in-one" microstimulator or other unit, such as a Bion® microstimulator manufactured by Advanced Bionics Corporation. In any case, stimulation source 12 controls the electrical stimulation pulses transmitted to electrodes 18 (which may be located on a stimulating portion 20 of an electrical stimulation lead 14), implanted proximate the network of peripheral nerve fibers, according to appropriate stimulation parameters (e.g., duration, amplitude or intensity, frequency, etc.). A doctor, the patient, or another user of stimulation source 12 may directly or indirectly input or modify stimulation parameters to specify or modify the nature of the electrical stimulation provided.

In one embodiment, as shown in FIG. 1A, stimulation source 12 includes an implantable pulse generator (IPG). An example IPG may be one manufactured by Advanced Neuromodulation Systems, Inc., such as the Genesis® System, part numbers 3604, 3608, 3609, and 3644. In another embodiment, as shown in FIG. 1B, stimulation source 12 includes an implantable wireless receiver. An example wireless receiver may be one manufactured by Advanced Neuromodulation Systems, Inc., such as the Renew® System, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary one or more stimulation parameters of the electrical stimulation pulses transmitted through electrical stimulation lead 14 to the stimulation site. An example wireless transmitter 122 may be one manufactured by Advanced Neuromodulation Systems, Inc., such as the Renew® System, part numbers 3508 and 3516.

As discussed above, instead or in addition to providing electrical stimulation, a neurological stimulation system may include an implantable infusion pump (not shown) and an implantable infusion catheter (not shown) with one or more infusion ports for the delivery of a medication or other suitable chemical to the network of peripheral nerve fibers located in and innervating the painful region of the low back area. In certain embodiments, appropriate infusion pumps 12a may include those illustrated and described in U.S. Pat. Nos. 4,772,263 and 6,666,845, which are hereby incorporated by reference herein as if fully illustrated and described herein. Where appropriate, an electrical stimulation lead 14 may be formed with a hollow inner channel and one or more infusion ports, and may be adapted for coupling to an infusion pump, thereby serving as a combined electrical stimulation lead and infusion catheter.

FIGS. 2A-2I illustrate example electrical stimulation leads 14 that may be used to stimulate peripheral nerves to treat low back pain. As described above, each of the one or more leads 14 that may be incorporated in stimulation system 10 includes electrodes 18 adapted to be positioned in tissue surrounding, overlying, or otherwise proximate the network of peripheral nerve fibers located in and innervating the painful region of the low back area and used to deliver electrical stimulation pulses to the network of peripheral nerve fibers located in and innervating the painful region of the low back area in response to receiving the electrical stimulation pulses from stimulation source 12. A percutaneous lead 14, such as example leads 14a-d, includes one or more circumferential electrodes 18 spaced apart from one another along the length of lead 14. Circumferential electrodes 18 emit electrical stimulation energy generally radially in all directions. A laminotomy or paddle style lead 14, such as example leads 14e-i, includes one or more directional electrodes 18 spaced apart from one another along one surface of lead 14. Directional electrodes 18 emit electrical stimulation energy in a direction generally perpendicular to the surface of lead 14 on which they are located, which may be desirable for directing the electrical stimulation in a particular direction to better target particular tissue. Although various types of leads 14 are shown as examples, the present invention contemplates stimulation system 10 including any suitable type of lead 14 in any suitable number. In addition, leads 14 may be used singly or in combination. For example, unilateral stimulation of the low back may be accomplished using a single lead 14 implanted in one side of the low back, while bilateral stimulation of the low back may be accomplished using two leads 14 implanted in opposite sides of the low back.

FIG. 3 illustrates example placement of the electrical stimulation system 10 shown in FIGS. 1A-1B within a person's body 30. Electrical stimulation lead 14 is implanted in or under the person's skin (i.e., in the epidermis, dermis, or subcutaneous tissue) surrounding, overlying, or otherwise proximate the network of peripheral nerve fibers located in and innervating the painful region of the low back area. In certain embodiments, electrical stimulation lead 14 is positioned such that one or more electrodes 18 are located superior to fascia overlying the network of peripheral nerve fibers located in and innervating the painful region of the low back area. Stimulation source 12 is implanted within a subcutaneous pocket within the person's torso (such as in or near the chest or buttocks), and connecting portion 16 is tunneled, at least in part, subcutaneously to connect stimulation source 12 with the electrical stimulation lead 14. However, stimulation source 12 may be located at any suitable location within the person's body according to particular needs. In certain embodiments, an implantable infusion catheter (not shown) and infusion pump (not shown) may be implanted in locations and in a manner analogous to implantation of electrical stimulation lead 14 and stimulation source 12. For example, similar to placement of electrodes 18 of an electrical stimulation lead 14, infusion ports of the infusion catheter may be located proximate the network of peripheral nerve fibers located in and innervating the painful region of the low back area.

FIG. 4 illustrates an example method for determining the location for electrical stimulation lead 14 and implanting the stimulation system 10 of FIGS. 1A-1B into a person for stimulating peripheral nerves to treat low back pain. At step 50, as further illustrated in FIG. 5A, a painful region 100 of the low back area is determined in consultation with the patient and marked or otherwise indicated on the person's body. As one example, the patient, the doctor, or another clinical professional may use a pen or other marker to mark painful region 100 of the low back area directly on the person's skin. As one other example, the doctor or another clinical professional may use a light fixture with an adjustable aperture to further illuminate painful region 100 of the low back area. In a particular embodiment, for optimal pain relief, electrical stimulation lead 14 is implanted in tissue surrounding, overlying, or otherwise proximate the network of peripheral nerve fibers located in and innervating a sub-region of the low back area, within region 100, that the patient identifies as being particularly sensitive to pain (i.e. having the greatest hyperalgesia). Thus, at step 52, as further illustrated in FIG. 5B, a sub-region 102 of the low back area that is particularly sensitive to pain is determined and sub-region 102 of the low back area is marked or otherwise indicated on the person's body. For example, the patient, the doctor, or another clinical professional may mark or otherwise indicate sub-region 102 in the same manner as region 100. Identifying sub-region 102 may include identifying an approximate epicenter of the pain within region 100. Pre-operatively, while the patient is positioned on the operating room table, the patient should preferably be asked to confirm the identification of sub-region 102 (including any identified epicenter), since the painful region or the spatial relationship between the marked skin and the painful region may move as a result of changes in position. Although example region 100 and sub-region are illustrated, the present invention contemplates any suitable regions 100 and sub-regions 102 according to particular circumstances. Preferably, the implant site of stimulation source 12 and the paths of the one or more electrical stimulation leads 14 are planned before implantation occurs. Consideration should preferably be made for avoiding the painful region to be treated or other regions of sensitivity.

At steps 54-58, electrical stimulation lead 14 is implanted in tissue surrounding, overlying, or otherwise proximate the network of peripheral nerve fibers located in and innervating painful region 100 of the low back area, preferably the network of peripheral nerve fibers located in and innervating sub-region 102 of the low back area. For example, electrical stimulation lead 14 may be implanted in the epidermis, the dermis, or the subcutaneous tissue proximate the network of peripheral nerve fibers located in and innervating sub-region 102 of the low back area. In a particular embodiment, electrical stimulation lead 14 is implanted approximately one centimeter deep, in a tissue plane lying between the dermal and subdermal layers. In general, the closer electrodes 18 are to the surface of the skin, the less likely the stimulation will cause contractions of the underlying muscles. Thus, implantation of electrical stimulation lead 14 more superficially to the subdermal layer (i.e., in the epidermis or dermis) may be desirable in other embodiments if unwanted stimulation of muscle nerve fibers is a concern. Preferably, electrical stimulation lead 14 will traverse region 100 such that the stimulation pulse electric field spans and provides effective stimulation over at least 90% of region 100 and 100% of sub-region 102. In a particular embodiment, an electrical stimulation lead 14 having four electrodes 18 may effectively span an area approximately the size of a tennis ball. If region 100 is too large for the effective span of electrodes 18, then optimal pain relief may not be realized. Preferably, electrical stimulation lead 14 should be placed such that it traverses the longest axis of region 100 and through the approximate center of sub-region 102 (including over any identified epicenter). Alternatively, if the patient is experiencing allodynia over region 100, then region 100 may need to be bracketed with two or more electrical stimulation leads 14 placed about the perimeter of region 100. Electrical stimulation lead 14 may be implanted percutaneously (either directly or through a suitable introducer where appropriate), surgically, or in any other manner.

Figure 5A:
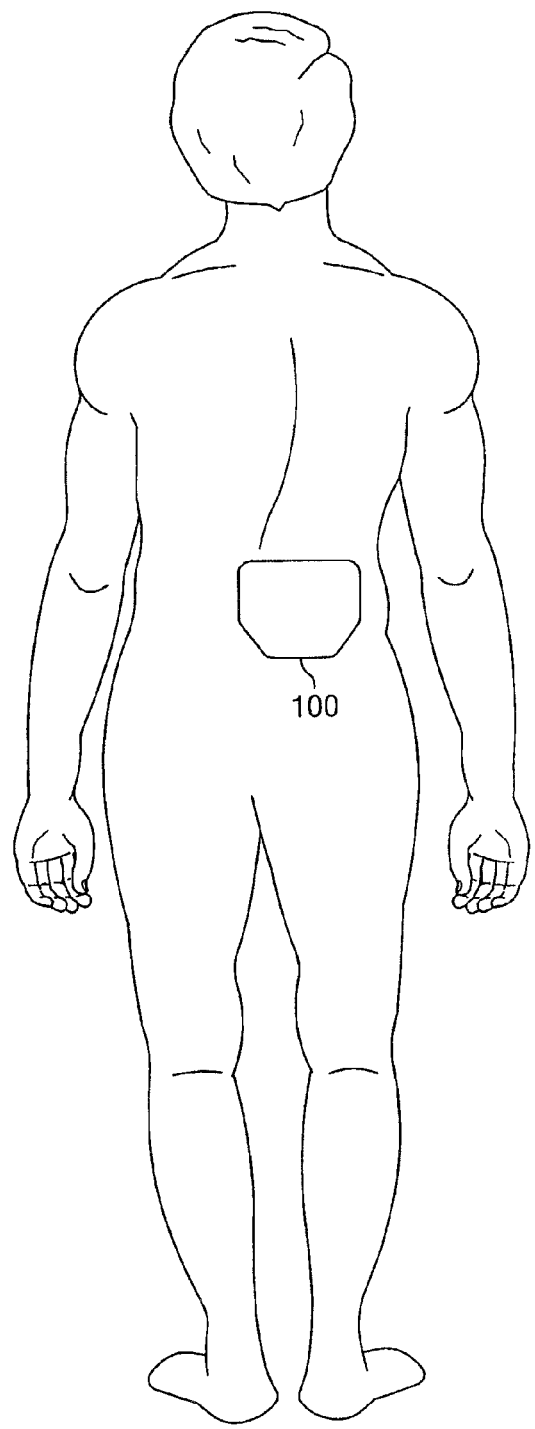
FIGS. 5A-5E further illustrate an example method for implanting the stimulation system of FIGS. 1A-1B into a person to stimulate peripheral nerves to treat low back pain.
Figure 5B:
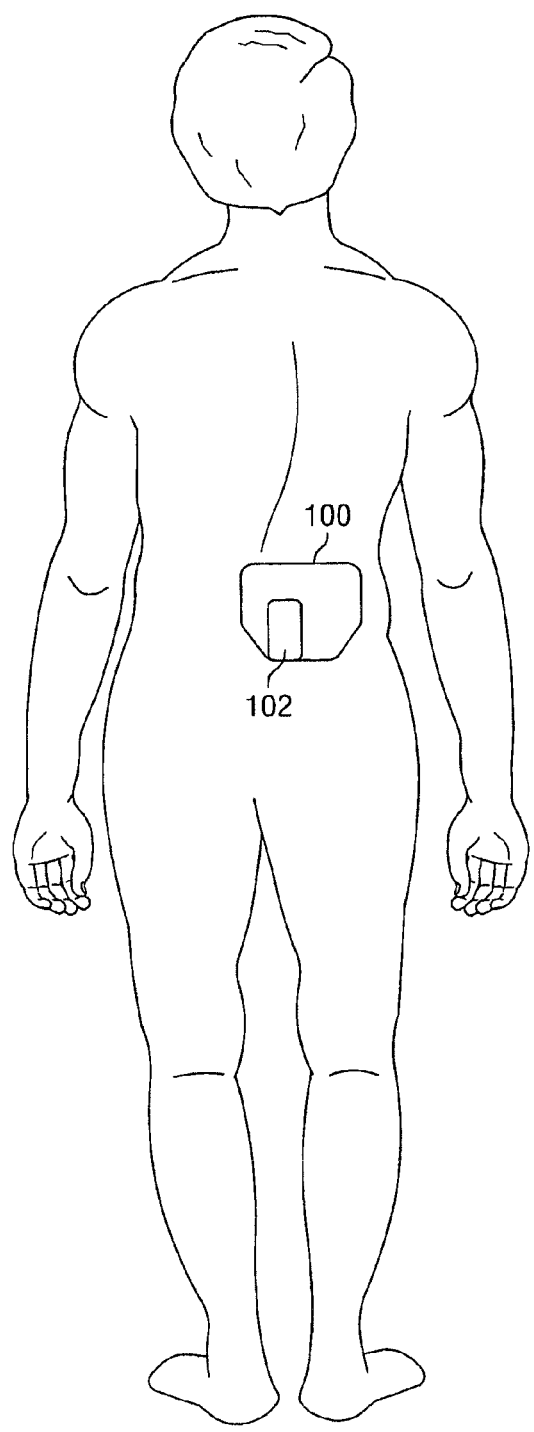
Figure 5C:
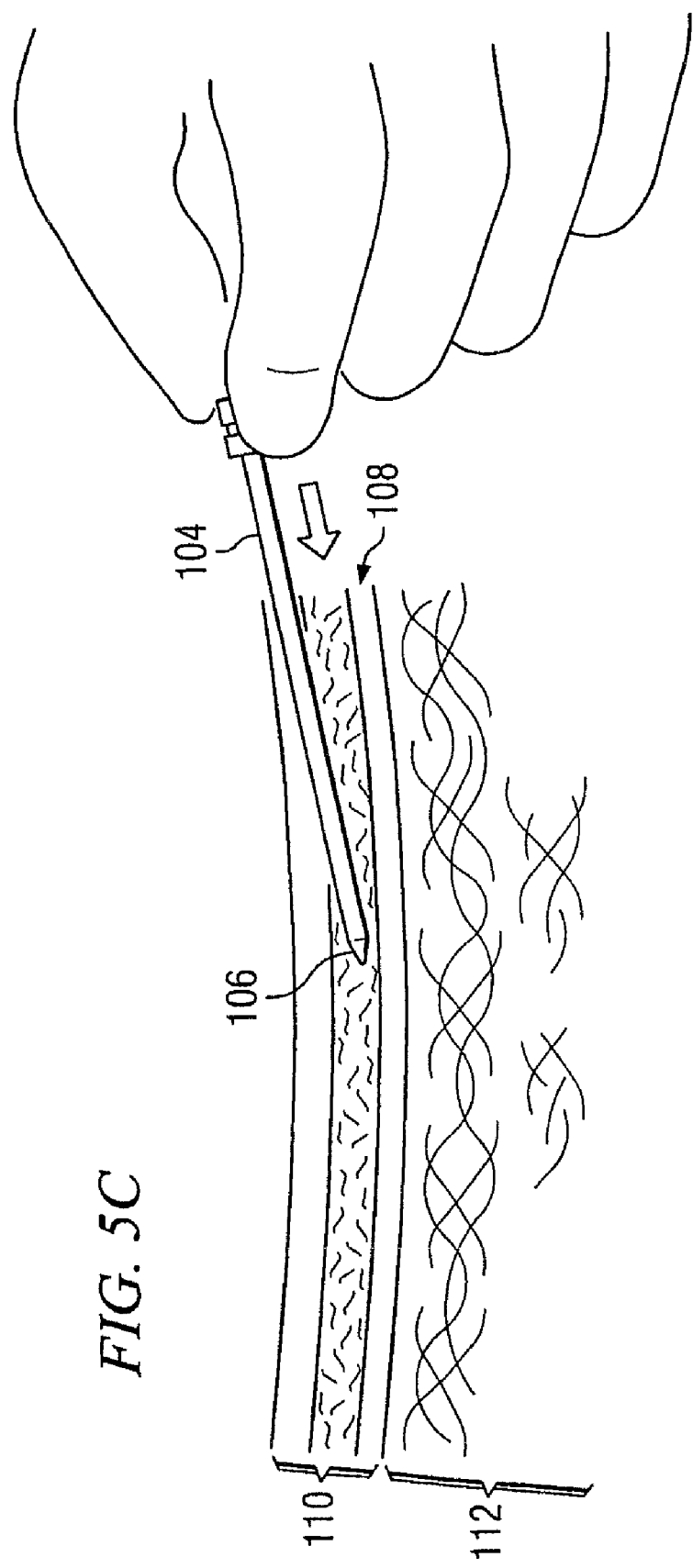

For example, at step 54 as further illustrated in FIG. 5C, a needle 104 may be inserted into sub-region 102 of the low back area such that tip 106 of needle 104 is located in the epidermis, the dermis, or the subcutaneous tissue (collectively, tissue 110) proximate the network of peripheral nerve fibers 112 located in and innervating sub-region 102. In the particular embodiment in which electrical stimulation lead 14 is implanted approximately one centimeter deep, in a tissue plain lying between the dermal and subdermal layers, needle 104 may visibly "tent" the skin as it is being advanced to the targeted implant site. In this particular embodiment, needle 104 should preferably advance with minimal resistance. If the resistance against needle 104 is too great, it may indicate that needle 104 is not in the proper tissue plane (i.e., is in the epidermal or dermal layer) or that the patient's epidermal or dermal layer is abnormally thick. Further, if needle 104 is in the epidermal or dermal layer, the skin may actually dimple at the needle insertion point and along the path to the targeted implant site. As discussed above, implantation of electrical stimulation lead 14 in the epidermal or dermal layer may be desirable in other particular embodiments where unwanted stimulation of muscle nerve fibers is a concern.

Figure 5D:
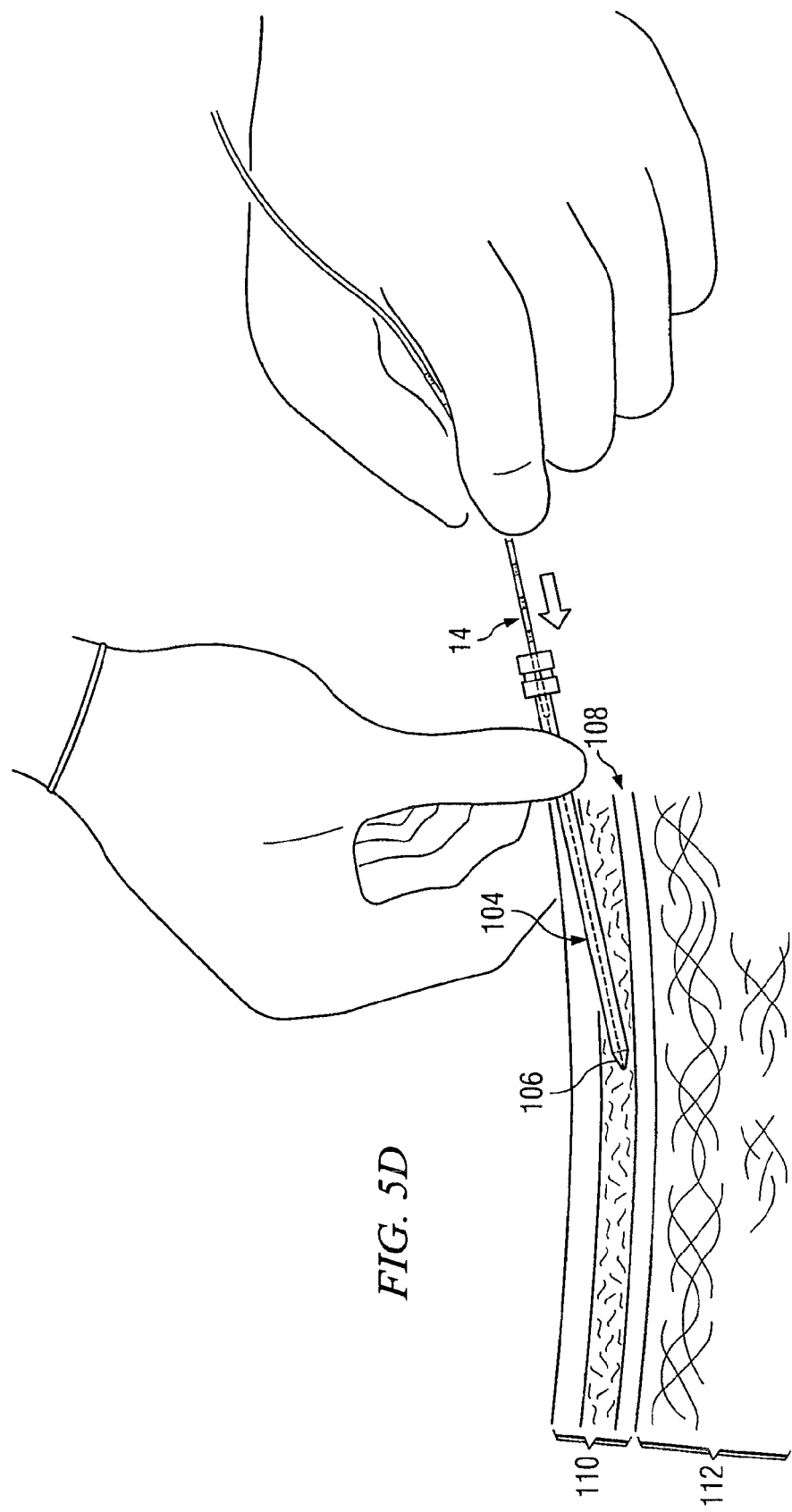

Continuing the example, at step 56 as further illustrated in FIG. 5D, electrical stimulation lead 14 may be inserted through needle 104 into sub-region 102 of the low back area such that electrodes 18 of lead 14 are located superior to fascia 108 or otherwise in tissue 110 proximate the network of peripheral nerve fibers 112 located in and innervating sub-region 102.

Figure 5E:
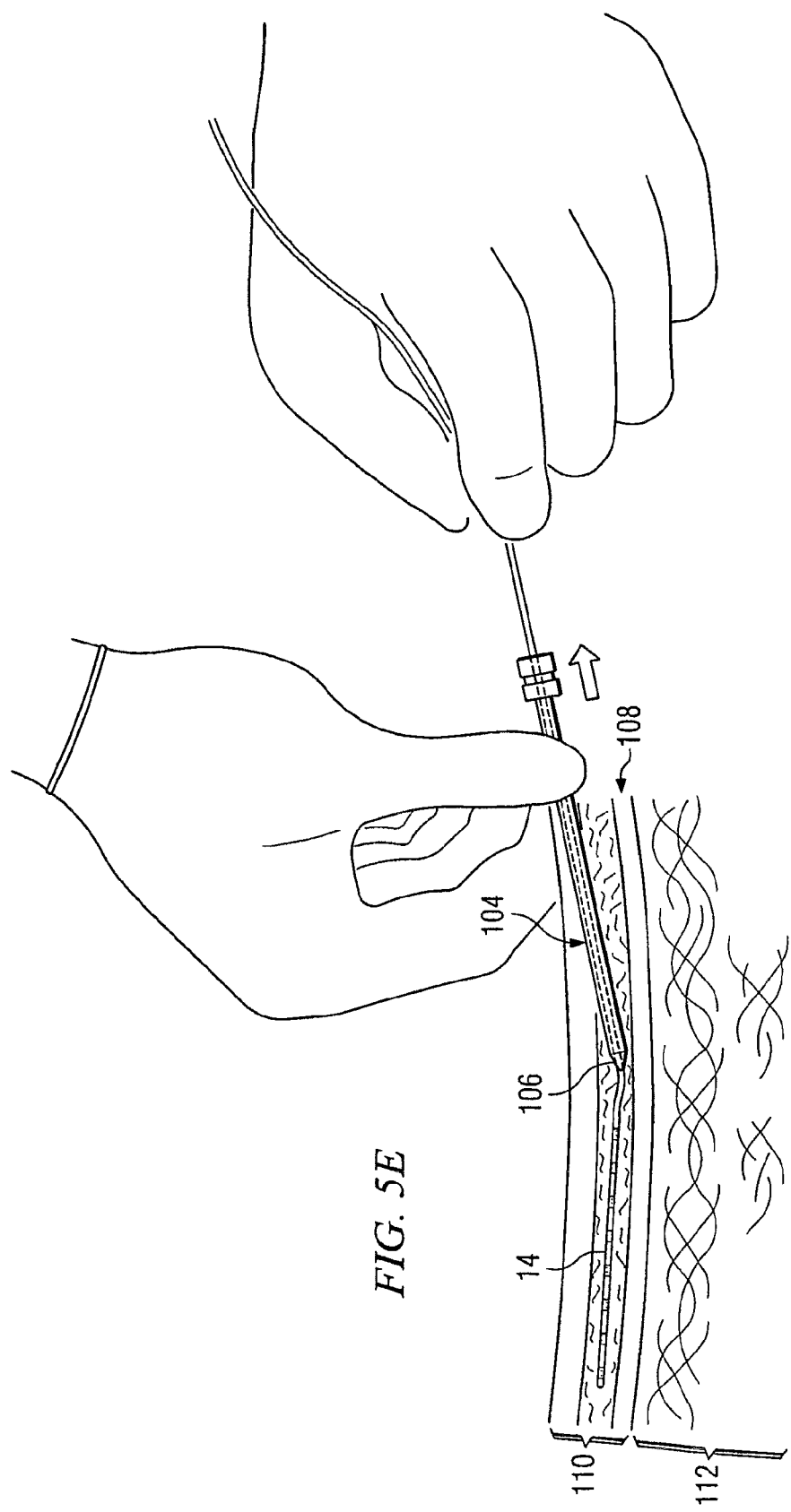

Continuing the example, at step 58 as further illustrated in FIG. 5E, needle 104 may then be removed leaving electrical stimulation lead 14 in position with electrodes 18 located superior to fascia 108 or otherwise in tissue 110 proximate the network of peripheral nerve fibers 112 located in and innervating sub-region 102.

As an alternative example, after needle 104 is inserted at step 54, a guide wire (not shown) may be inserted through needle 104 into position, needle 104 may be removed, an introducer (not shown) may be advanced along the guide wire into position, electrical stimulation lead 14 may be inserted through the introducer into position, and the introducer may then be removed leaving lead 14 in position with electrodes 18 again located superior to fascia 108 or otherwise in tissue 110 proximate the network of peripheral nerve fibers 112 located in and innervating sub-region 102.

Preferably, electrical stimulation lead 14 should be anchored using a suitable anchoring technique. Anchoring electrical stimulation lead 14 for peripheral nerve stimulation may be a challenge due to the slight differences between the anatomies of patients, in particular the tissue planes in which electrical stimulation lead 14 is to be implanted. In contrast, anchoring an electrical stimulation lead 14 used for spinal cord stimulation as it exits the epidural space may be more straightforward. In a particular embodiment, two anchors are utilized to anchor electrical stimulation lead 14—a "butterfly" anchor such as one manufactured by Advanced Neuromodulation Systems, Inc., part number 64-1105, and a "long" anchor such as one manufactured by Advanced Neuromodulation Systems, Inc., part number 64-1106. After lead placement is finalized, a small incision is made at the point where needle 104 exits the skin and dissection is performed down to the fascial plane. The wings or tabs of the butterfly anchor are cut off and the butterfly anchor is placed on the lead body and sutured to the dermal or subdermal tissue layer superficially and perpendicular to the surface of the skin. The long anchor is then threaded onto electrical stimulation lead 14. Electrical stimulation lead 14 is looped around to the fascial surface with the long anchor positioned flat against the fascial plane and then sutured to the fascia. Once the anchors have been secured, preferably after complete implantation of electrical stimulation lead 14 and stimulation source 12, the anchoring pocket can be closed. Although a particular anchoring technique is described in detail, other embodiments may involve other suitable anchoring techniques according to particular needs.

At step 60, stimulation source 12 is activated, which generates and sends electrical stimulation pulses for delivery via electrodes 18 to the network of peripheral nerve fibers 112 located in and innervating sub-region 102 of the low back area. A doctor, the patient, or another user of stimulation source 12 may directly or indirectly input or modify one or more stimulation parameters to specify or modify the nature of the stimulation provided. At step 62, the person indicates whether the low back pain is partially or completely suppressed by electrical stimulation system 10. In certain embodiments, the patient may or may not experience paresthesia. For example, the electrical stimulation might not stimulate the network of peripheral nerve fibers 112 located in and innervating sub-region 102 of the low back area to an extent necessary to cause paresthesia or might not stimulate nerve fibers that would need to be stimulated to cause paresthesia. If the low back pain is not adequately suppressed, electrical stimulation lead 14 may be moved incrementally at step 64 until the person indicates that the low back pain is adequately suppressed. Once electrical stimulation lead 14 has been properly positioned such that the low back pain is adequately suppressed, stimulation source 12 is implanted at step 66. Stimulation source 12 may be implanted before, after, or even without such a trial stimulation period, according to particular needs. In certain embodiments, trial peripheral nerve stimulation can be performed over a longer period of time, up to thirty days for example, than trial spinal cord stimulation due to a reduced risk of complications. For example, in a particular embodiment in which electrical stimulation lead 14 is implanted in a tissue plain lying between the dermal and subdermal layers, subsequent sequela such as infections are rare and, when they occur, can be easily managed. A longer trial stimulation period may give the patient a longer opportunity to become accustomed to the stimulation sensation, a longer period in which to initiate repositioning of the lead if necessary, and a longer opportunity to try different stimulation programs to optimize the pain relief. Of course, if after an extended trial stimulation period the patient continues to describe the stimulation sensation as uncomfortable or bothersome, then the trial should be considered unsuccessful and another course of therapy considered.

The implant site is typically a subcutaneous pocket formed to receive and house stimulation source 12. The implant site is usually positioned a distance away from the insertion site, such as in the chest, buttocks, or another suitable location. However, a suitably small stimulation source 12 may be used to allow stimulation source 12 to be implanted at or very near the stimulation site. Connecting portion 16 of electrical stimulation lead 14 extends from the lead insertion site to the implant site at which stimulation source 12 is implanted. Where appropriate, an extension may be used to connect electrical stimulation lead 14 to stimulation source 12. A doctor, the patient, or another user of stimulation source 12 may thereafter directly or indirectly input or modify one or more stimulation parameters to specify the nature of the stimulation provided.

In certain embodiments, an implantable infusion catheter (not shown) and infusion pump (not shown) may be implanted in locations and in a manner analogous to implantation of electrical stimulation lead 14 and stimulation source 12. For example, similar to placement of electrodes 18 of an electrical stimulation lead 14, one or more infusion ports of the infusion catheter may be located superior to fascia 108 or otherwise in tissue 110 proximate the network of peripheral nerve fibers 112 located in and innervating sub-region 102 of the low back area. Where appropriate, an electrical stimulation lead 14 may be formed with a hollow inner channel and one or more infusion ports, and may be adapted for coupling to an infusion pump, thereby serving as a combined electrical stimulation lead and infusion catheter.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example stimulation system 10 into a person for electrical stimulation to treat low back pain.

Figure 6:
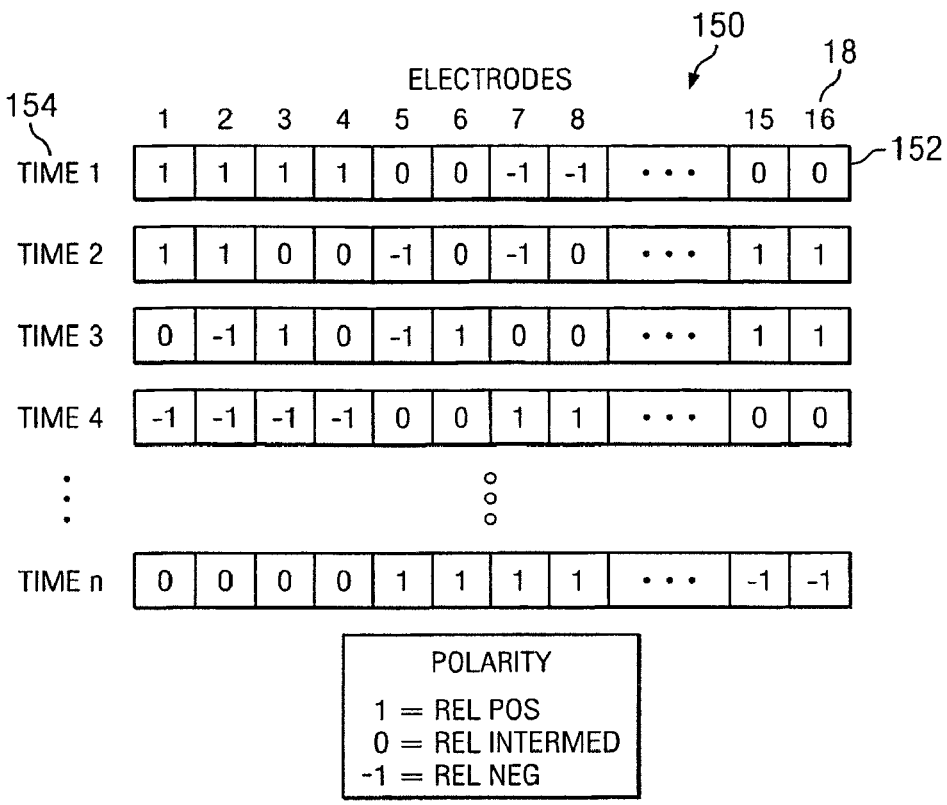
FIG. 6 illustrates an example stimulation set.

FIG. 6 illustrates an example stimulation set 150. One or more stimulation sets 150 may be provided, each stimulation set 150 specifying a number of stimulation parameters for stimulation set 150. For example, as described more fully below with reference to FIGS. 7-8, multiple stimulation sets 150 may be executed in an appropriate sequence according to a pre-programmed or randomized stimulation program. Stimulation parameters for a stimulation set 150 may include an amplitude or intensity, a frequency, phase information, and a pulse width for each of a series of stimulation pulses that electrodes 18 are to deliver to the network of peripheral nerve fibers located in and innervating the painful region of the low back area during a time interval during which stimulation set 150 is executed, along with a polarity 152 for each electrode 18 in each stimulation pulse. In general, electric fields are generated between adjacent electrodes 18 having different polarities 152 to deliver electrical stimulation pulses to the network of peripheral nerve fibers located in and innervating the painful region of the low back area. Stimulation parameters may also include a pulse shape, for example, biphasic cathode first, biphasic anode first, or any other suitable pulse shape.

Figure 7:
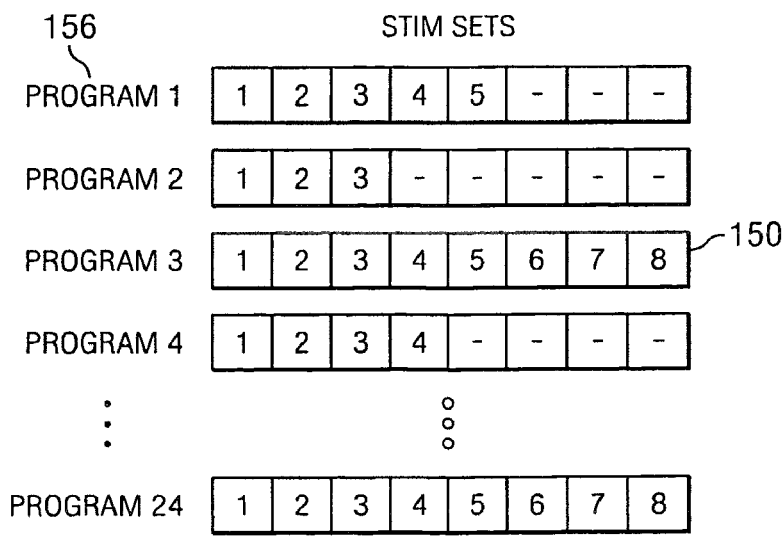
FIG. 7 illustrates a number of example stimulation programs, each of which includes a number of stimulation sets.

The polarity for an electrode 18 at a time 154 beginning a corresponding stimulation pulse or sub-interval within a stimulation pulse may be a positive polarity 152 such that current flows out of the electrode 18 into the tissue (from which the current will return through one or more other electrodes 18), a negative polarity 152 such that current flows into the electrode 18 from the tissue (into which the current was delivered from one or more other electrodes 18), or a zero (i.e., "high impedance) polarity such that the electrode 18 is essentially "turned off" and zero or substantially zero current flows out of or into the electrode 18. Thus, the polarity 152 of an electrode determines whether current will flow through the electrode 18 and in which direction. In certain embodiments, the polarity 152 of an electrode 18 may be defined in terms of voltage, in which case the polarity 152 may be relatively positive polarity 152, a relatively negative polarity 152, or an intermediate polarity 152 between the relatively positive polarity 152 and relatively negative polarity 152. For example, the relatively positive polarity 152 may involve a positive voltage, the relatively negative polarity 152 may involve a negative voltage, and the relatively intermediate polarity 152 may involve a zero voltage. As another example, the relatively positive polarity 152 may involve a first negative voltage, the relatively negative polarity 152 may involve a second negative voltage more negative than the first negative voltage, and the relatively intermediate polarity 152 may involve a negative voltage between the first and second negative voltages. The availability of three distinct polarities 152 for an electrode 18 may be referred to as "tri-state" electrode operation. The polarity 152 for each electrode 18 may change for each of the sequence of times 154 corresponding to stimulation pulses or to sub-intervals within a stimulation pulse according to the stimulation parameters specified for the stimulation set 150. For example, as is illustrated in FIG. 7 for an example stimulation set 150 for a stimulation lead 14 with sixteen electrodes 18, the polarities 152 of the sixteen electrodes 18 may change for each of the sequence of times 154. In the example of FIG. 7, a positive or relatively positive polarity 152 is represented using a "1," a negative or relatively negative polarity 152 is represented using a "–1," and a zero or relatively intermediate polarity 152 is represented using a "0," although any suitable values or other representations may be used.

Figure 8:
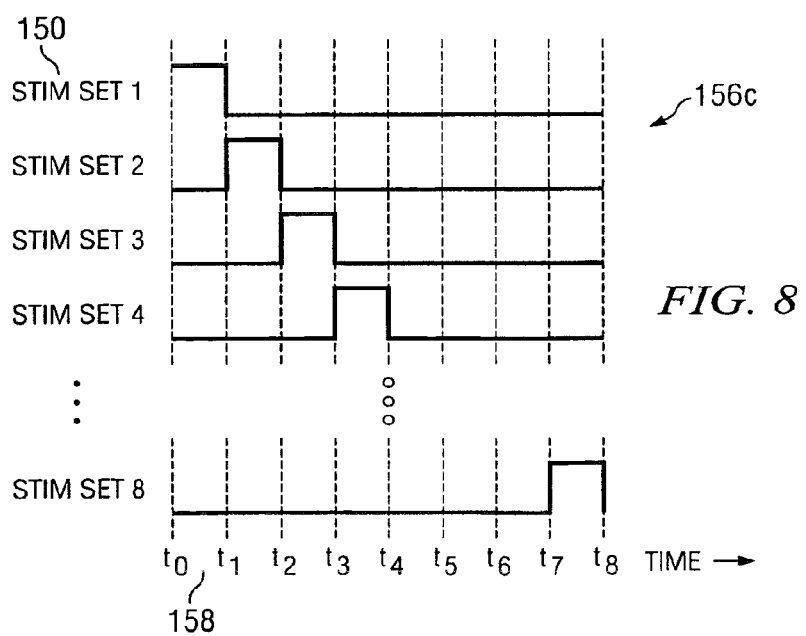
FIG. 8 illustrates example execution of a sequence of stimulation sets within an example stimulation program.
Figure 2A:
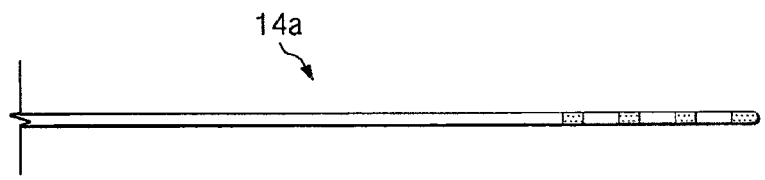
FIGS. 2A-2I illustrate example electrical stimulation leads that may be used to stimulate peripheral nerves to treat low back pain.
Figure 2B:
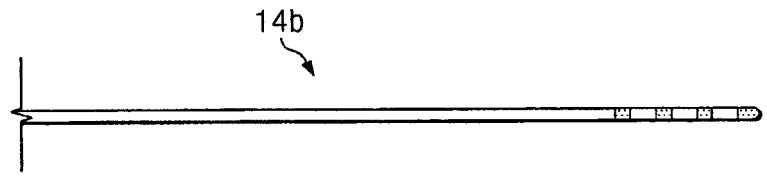
Figure 2C:
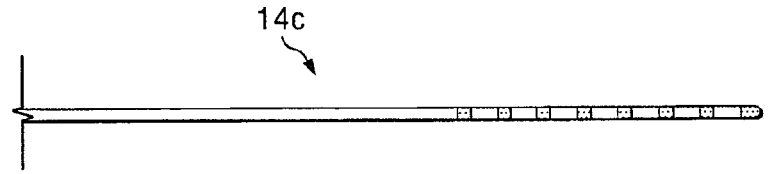
Figure 2D:
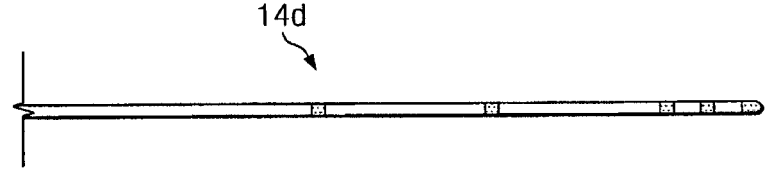
Figure 2E:
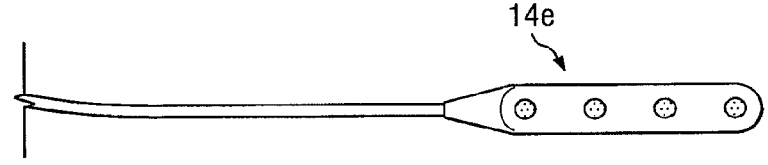
Figure 2F:
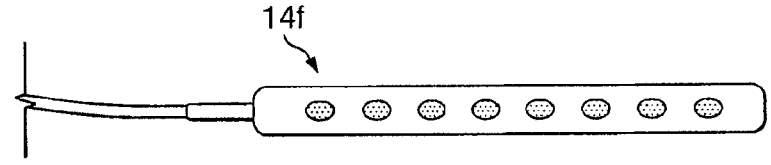
Figure 2G:
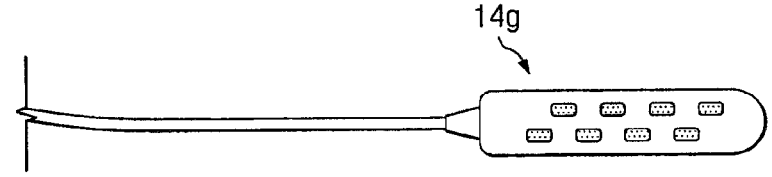
Figure 2H:
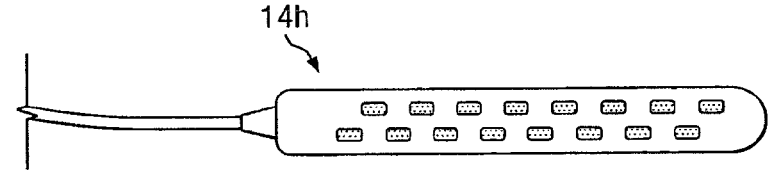
Figure 2I:
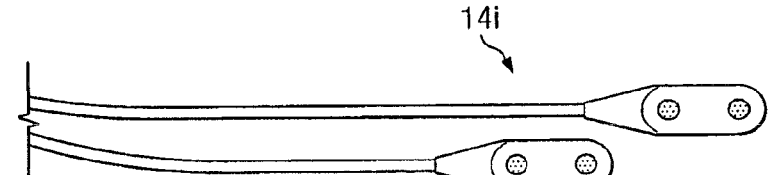

FIG. 7 illustrates a number of example stimulation programs 156, each including a number of stimulation sets 150. As described above, each stimulation set 150 specifies a number of stimulation parameters for stimulation set 150. In one embodiment, in each stimulation program 156, stimulation system 10 consecutively executes the sequence of one or more stimulation sets 150 associated with stimulation program 156. The sequence may be executed only once, repeated a specified number of times, or repeated an unspecified number of times within a specified time period. For example, as is illustrated in FIG. 8 for the third example stimulation program 156c including eight stimulation sets 150, each of the eight stimulation sets 150 is consecutively executed in sequence. Although the time intervals 158 ($t_1$-$t_0$, $t_2$-$t_1$, etc.) during which the stimulation sets 150 are executed are shown as being equal, the present invention contemplates a particular stimulation set 150 being executed over a different time interval 158 than one or more other stimulation sets 150 according to particular needs.

Although stimulation system 10 is illustrated by way of example as accommodating up to twenty-four stimulation programs 156 each including up to eight stimulation sets 150, the present invention contemplates any appropriate number of stimulation programs 156 each including any appropriate number of stimulation sets 150. For example, in a very simple case, a single stimulation program 156 may include a single stimulation set 150, whereas in a very complex case more than twenty-four stimulation programs 156 may each include more than eight stimulation sets 150.

In one embodiment, stimulation system 10 executes only a single stimulation program 156 in response to user selection of that stimulation program for execution. In another embodiment, during a stimulation period, stimulation system 10 executes a sequence of pre-programmed stimulation programs 156 for each lead 14 until the stimulation period ends. Depending on the length of the stimulation period and the time required to execute a sequence of stimulation programs 156, the sequence may be executed one or more times. For example, the stimulation period may be defined in terms of a predetermined number of cycles each involving a single execution of the sequence of stimulation programs 156, the sequence of stimulation programs 156 being executed until the predetermined number of cycles has been completed. As another example, the stimulation period may be defined in terms of time, the sequence of stimulation programs 156 being executed until a predetermined time interval has elapsed or the patient or another user manually ends the stimulation period. Although a sequence of stimulation programs 156 is described, the present invention contemplates a single stimulation program being executed one or more times during a stimulation period according to particular needs. Furthermore, the present invention contemplates each stimulation program 156 being executed substantially immediately after execution of a previous stimulation program 156 or being executed after a suitable time interval has elapsed since completion of the previous stimulation program 156. Where stimulation system 10 includes multiple leads 14, stimulation programs 156 for a particular lead 14 may be executed substantially simultaneously as stimulation programs 156 for one or more other leads 14, may be alternated with stimulation programs 156 for one or more other leads 14, or may be arranged in any other suitable manner with respect to stimulation programs 156 for one or more other leads 14.

In general, each stimulation program 156 may, but need not necessarily, be set up for electrical stimulation of a different network of peripheral nerve fibers located in and innervating the painful region of the low back area. For example, one or more stimulation programs 156 may be set up for therapeutic electrical stimulation of one network of peripheral nerve fibers located in and innervating the painful region of the low back area and one or more other stimulation programs 156 may be set up for electrical stimulation of another network of peripheral nerve fibers located in and innervating the painful region of the low back area to improve the overall pain relief provided.

The present invention contemplates any suitable circuitry within stimulation source 12 for generating and transmitting signals for electrical stimulation of peripheral nerves to treat low back pain. Example circuitry which may be used is illustrated and described in U.S. Pat. No. 6,609,031 B1, which is hereby incorporated by reference herein as if fully illustrated and described herein.

Although the present invention has been described above in connection with several embodiments, a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A method for treating low back pain, comprising:
   identifying a region of low back pain in a patient;
   identifying a sub-region having an approximate epicenter of pain within the region;
   implanting one or more stimulation leads with a plurality of electrodes being disposed in the sub-region having an approximate epicenter of pain and substantially aligned along a greatest axis of the region of low back pain, wherein implanting comprises positioning the plurality of electrodes in the epidermis, dermis, or subcutaneous tissue superior to fascia containing a network of localized peripheral nerve fibers located in and influencing the painful region of the low back area without regard to a specific or identifiable nerve or nerve branch;
   generating electrical pulses using an implantable pulse generator implanted in the patient, the implantable pulse generator being electrically coupled to the one or more stimulation leads; and
   treating the patient's low back pain by applying the generated electrical pulses from the implantable pulse generator to the plurality of electrodes to stimulate the network of localized peripheral nerve fibers located in and influencing the painful region of the low back pain.

2. The method of claim 1, wherein the implanting positions an electrode of the plurality of electrodes immediately proximate to an epicenter of pain.

3. The method of claim 2, further comprising indicating the painful region of the person's low back area on the person's body using a marking system prior to implanting the electrodes.

4. The method of claim 1, wherein the stimulation source generates the stimulation pulses according to one or more stimulation sets each specifying a plurality of stimulation parameters to relieve pain in the painful region of the patient's low back area.

5. The method of claim 4, wherein the stimulation parameters for a stimulation set comprising a polarity for each electrode at each of one or more times within a stimulation pulse for the stimulation set.

6. The method of claim 1, wherein the stimulation source generates the stimulation pulses according to a plurality of stimulation programs each comprising one or more stimulation sets, each stimulation set specifying a plurality of stimulation parameters to relieve pain in the painful region of the patient's low back area.

7. The method of claim 1, wherein the electrical stimulation pulses of the network of localized peripheral nerve fibers provides paresthesia with respect to the painful region of the patient's low back area.

* * * * *